United States Patent
Blazecka et al.

(10) Patent No.: US 9,359,374 B2
(45) Date of Patent: Jun. 7, 2016

(54) POLYMORPHIC FORMS OF RIFAXIMIN

(71) Applicant: APOTEX PHARMACHEM INC., Brantford (CA)

(72) Inventors: Peter Garth Blazecka, Brantford (CA); Nageib Mohamed, Oakville (CA); Cameron L. McPhail, Brantford (CA); Sammy Chris Duncan, Brantford (CA); Randa E. El-Haj, Brantford (CA); Yajun Zhao, Brantford (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 0 days.

(21) Appl. No.: 14/408,251

(22) PCT Filed: Jun. 13, 2013

(86) PCT No.: PCT/CA2013/000562
§ 371 (c)(1),
(2) Date: Dec. 15, 2014

(87) PCT Pub. No.: WO2013/185211
PCT Pub. Date: Dec. 19, 2013

(65) Prior Publication Data
US 2015/0284407 A1 Oct. 8, 2015

Related U.S. Application Data

(60) Provisional application No. 61/659,422, filed on Jun. 13, 2012.

(51) Int. Cl.
*C07D 498/22* (2006.01)
*C07D 491/22* (2006.01)

(52) U.S. Cl.
CPC ............ *C07D 491/22* (2013.01); *C07D 498/22* (2013.01)

(58) Field of Classification Search
CPC ...................................................... C07D 498/22
See application file for complete search history.

(56) References Cited

U.S. PATENT DOCUMENTS

| | | | |
|---|---|---|---|
| 4,557,866 A | 12/1985 | Cannata et al. | |
| 7,045,620 B2 | 5/2006 | Viscomi et al. | |
| 7,612,199 B2 | 11/2009 | Viscomi et al. | |
| 7,709,634 B2 | 5/2010 | Kothakonda et al. | |
| 7,906,542 B2 | 3/2011 | Viscomi et al. | |
| 7,915,275 B2 | 3/2011 | Viscomi et al. | |
| 8,883,795 B2 * | 11/2014 | Kothakonda | C07D 498/22 514/254.11 |
| 2005/0272754 A1 | 12/2005 | Viscomi et al. | |

(Continued)

FOREIGN PATENT DOCUMENTS

| | | |
|---|---|---|
| CA | 2538546 A1 | 5/2005 |
| CA | 2800668 A1 | 12/2011 |

(Continued)

*Primary Examiner* — Bruck Kifle
(74) *Attorney, Agent, or Firm* — The Webb Law Firm

(57) ABSTRACT

Provided for in the instant application are two additional forms of rifaximin, namely rifaximin polymorphic forms APO-III and APO-IV. Also provided are allegedly novel processes for preparing the previously disclosed rifaximin polymorphic forms APO-I and APO-II. Rifaximin is a non-aminoglycoside antibiotic that has previously been found to be useful for the treatment of traveller's diarrhea caused by *Escherichia coli* bacteria, as well as in the treatment of irritable bowel syndrome, diverticular disease, hepatic encephalopathy, pyogenic skin infections and as an antibacterial prophylactic prior to colon surgery.

25 Claims, 7 Drawing Sheets

(56) References Cited

U.S. PATENT DOCUMENTS

| | | |
|---|---|---|
| 2008/0262024 A1 | 10/2008 | Viscomi et al. |
| 2008/0262220 A1 | 10/2008 | Viscomi et al. |
| 2008/0262232 A1 | 10/2008 | Viscomi et al. |
| 2009/0082558 A1 | 3/2009 | Kothakonda et al. |
| 2009/0130201 A1 | 5/2009 | Viscomi et al. |
| 2009/0312357 A1 | 12/2009 | Rao et al. |
| 2010/0010028 A1 | 1/2010 | Maffei et al. |

FOREIGN PATENT DOCUMENTS

| | | | |
|---|---|---|---|
| CA | 2802874 | A1 | 12/2011 |
| CA | 2825964 | A1 | 8/2012 |
| JP | 2013184902 | A | 9/2013 |
| WO | 2008155728 | A1 | 12/2008 |
| WO | 2009108730 | A2 | 9/2009 |
| WO | 2011080691 | A1 | 7/2011 |
| WO | 2011103120 | A1 | 8/2011 |
| WO | 2011156897 | A2 | 12/2011 |
| WO | 2012035544 | A2 | 3/2012 |
| WO | 2012150561 | A1 | 11/2012 |
| WO | 2012156533 | A1 | 11/2012 |
| WO | 2012156954 | A1 | 11/2012 |
| WO | 2013027227 | A1 | 2/2013 |

\* cited by examiner

POLYMORPHIC FORMS OF RIFAXIMIN

TECHNICAL FIELD

The present invention relates to polymorphic forms of Rifaximin and to methods for their preparation.

BACKGROUND

Rifaximin (1) is a non-aminoglycoside semi-synthetic, nonsystemic antibiotic derived from Rifamycin, useful for the treatment of traveler's diarrhea in adults and in children 12 years of age and older caused by *Escherichia coli* bacteria. Rifaximin has also been evaluated for the treatment of irritable bowel syndrome, diverticular disease, hepatic encephalopathy, pyogenic skin infections, and as an antibacterial prophylactic prior to colon surgery. Chemically, Rifaximin is (2S,16Z,18E,20S,21S,22R,23R,24R,25S,26S,27S, 28E)-5, 6,21,23,25-pentahydroxy-27-methoxy-2,4,11,16,20,22,24, 26-octamethyl-2,7-(epoxypentadeca-[1,11,13]trienimino)-benzofuro[4,5-e]-pyrido[1,2-(a)]-benzimidazole-1,15(2H) dione, 25-acetate.

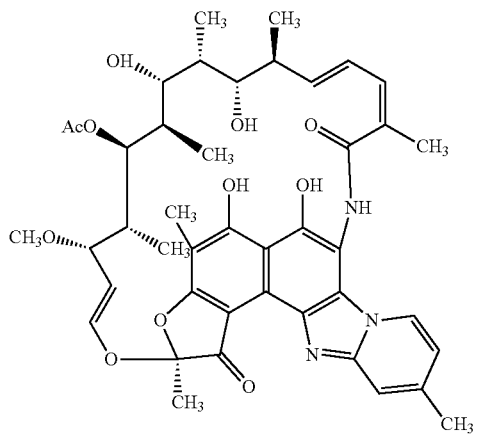

(1) Rifaximin

Rifaximin is currently sold in the US under the brand name Xifaxan™ by Salix Pharmaceuticals. It is also sold in Europe under the names Spiraxin™ Zaxine™, Normix™ and Rifacol™ and in India under the name Rifagut™.

U.S. Pat. No. 4,557,866 describes a new process for the synthesis of pyrido-imidazo-rifamycins. The process comprises reacting the rifamycin 0 with a 2-aminopyridine.

U.S. Pat. No. 7,045,620, U.S. Pat. No. 7,612,199, US 20080262220 and US 20080262232 disclose crystalline polymorphous forms of Rifaximin (INN) antibiotic named Rifaximin alpha and Rifaximin beta, and a poorly crystalline form named Rifaximin gamma. These forms can be obtained by means of a crystallization process carried out by hot-dissolving the raw Rifaximin in ethyl alcohol and by causing the crystallization of the product by the addition of water at a determinate temperature and for a determinate time period. The crystallization is followed by drying carried out under controlled conditions until specific water content is reached in the end product.

US 20080262024 describes a composition comprising substantially amorphous Rifaximin, and a method of preparing amorphous Rifaximin. The method comprises providing dried Rifaximin; heating the Rifaximin in the presence of an alcohol to result in dissolution of the Rifaximin; precipitating and drying the precipitate to have a water content of less than 2% to form substantially amorphous Rifaximin.

US 20050272754 relates to Rifaximin polymorphic forms alpha, beta and gamma, the processes for their preparation and the use thereof in the manufacture of medicinal preparations for the oral or topical route.

WO 2008155728 describes a process which enables Rifaximin in a completely amorphous form to be obtained. Said process comprises the steps of dissolving crude Rifaximin in absolute ethanol while hot and then collecting after precipitation by cooling the title compound in amorphous form.

US 20090312357 discloses amorphous Rifaximin, methods of making it, and pharmaceutical compositions containing it. Also described are methods of converting amorphous Rifaximin to crystalline Rifaximin and vice versa.

WO 2009108730 relates to Rifaximin polymorphic, salt, hydrate, and amorphous forms, to their use in medicinal preparations, and to therapeutic methods using them. Form zeta, Form eta, Form alpha-dry, Form i, Form beta-1, Form beta-2, Form epsilon-dry, and amorphous forms of Rifaximin as well as a mesylate salt are described.

US 20090082558 describes a stable amorphous form of Rifaximin. This form is chemically and polymorphic stable on storage and can be prepared by dissolving Rifaximin in a solvent to form a solution which is precipitated by adding an anti-solvent and isolating of the precipitated amorphous Rifaximin as an end product.

US 20090130201 describes crystalline polymorphous forms of Rifaximin (INN) antibiotic named Rifaximin delta and Rifaximin epsilon useful in the production of medicinal preparations containing Rifaximin for oral and topical use and obtained by means of a crystallization process carried out by hot-dissolving the raw Rifaximin in ethyl alcohol and by causing the crystallization of the product by addition of water at a determinate temperature and for a determinate time period, followed by drying carried out under controlled conditions until reaching a settled water content in the end product.

US 20100010028 describes polyols which stabilize polymorphous forms of Rifaximin, in particular the beta form. When polyols having at least two hydroxyl groups are added to Rifaximin powder, polymorph beta is stable and remains stable in time independently from the environment humidity. A method to prepare formulations constituted by pure and stable polymorphous forms able to give a pharmaceutical product is also described.

SUMMARY

The present invention relates, at least in part, to processes for the preparation of crystalline forms of Rifaximin, namely polymorphic forms of Rifaximin termed herein as APO-I and APO-II as well as intermediate polymorphic forms of said processes termed herein as APO-III and APO-IV.

Illustrative embodiments of the present invention provide the polymorphic form APO-III of Rifaximin.

Illustrative embodiments of the present invention provide the polymorphic form APO-III of Rifaximin described herein characterized by a PXRD diffractogram comprising peaks, in terms of degrees 2-theta, at approximately 7.1, 8.4, 9.1, 11.6, 13.1, 15.3, 16.4, 18.5, 18.8, 19.4 and 25.0.

Illustrative embodiments of the present invention provide the polymorphic form APO-III of Rifaximin described herein characterized by a PXRD diffractogram comprising peaks, in terms of degrees 2-theta, at approximately 7.1, 8.4, 11.6, 13.1, 18.5, 18.8, and 25.0.

Illustrative embodiments of the present invention provide the polymorphic form APO-III of Rifaximin described herein characterized by a PXRD diffractogram substantially similar to the PXRD diffractogram as depicted in FIG. 5.

Illustrative embodiments of the present invention provide the polymorphic form APO-III of Rifaximin described herein characterized by a PXRD diffractogram as depicted in FIG. 5.

Illustrative embodiments of the present invention provide the polymorphic form APO-III of Rifaximin described herein characterized by a 1% KBr FTIR spectrum comprising peaks, in terms of $cm^{-1}$, at approximately 3427, 2968, 2934, 1714, 1648, 1588, 1506, 1373, 1338, 1226, 1158, and 1124.

Illustrative embodiments of the present invention provide the polymorphic form APO-III of Rifaximin described herein characterized by a 1% KBr FTIR spectrum comprising peaks, in terms of $cm^{-1}$, at approximately 2968, 2934, 1714, 1506 and 1124.

Illustrative embodiments of the present invention provide the polymorphic form APO-III of Rifaximin described herein characterized by a FTIR spectrum substantially similar to the FTIR spectrum as depicted in FIG. 6.

Illustrative embodiments of the present invention provide the polymorphic form APO-III of Rifaximin described herein characterized by a FTIR spectrum as depicted in FIG. 6.

Illustrative embodiments of the present invention provide a process for preparation of a polymorphic form APO-III of Rifaximin, the process comprising:
  i. displacing a first organic solvent with water from a polymorphic form APO-II of Rifaximin to produce a damp cake; and
  ii. drying the damp cake until a water content of between about 0.5% to about 2% is reached.

Illustrative embodiments of the present invention provide a process for preparation of a polymorphic form APO-III of Rifaximin described herein wherein the first organic solvent is selected from the group consisting of ethyl acetate, dichloromethane, isopropanol, n-butanol, acetonitrile, heptanes and mixtures thereof.

Illustrative embodiments of the present invention provide a process for preparation of a polymorphic form APO-III of Rifaximin described herein wherein the first organic solvent is ethyl acetate.

Illustrative embodiments of the present invention provide a process for preparation of a polymorphic form APO-III of Rifaximin described herein wherein the displacing a first organic solvent with water is performed by washing a polymorphic form APO-II of Rifaximin with water.

Illustrative embodiments of the present invention provide a process for preparation of a polymorphic form APO-III of Rifaximin described herein wherein the displacing a first organic solvent with water is performed by suspending or pulping a polymorphic form APO-II of Rifaximin in water.

Illustrative embodiments of the present invention provide a process for preparation of a polymorphic form APO-III of Rifaximin described herein wherein the damp cake has a water content of from about 20% to about 50%.

Illustrative embodiments of the present invention provide a process for preparation of a polymorphic form APO-III of Rifaximin described herein wherein the drying is conducted under vacuum or using a fluid bed dryer.

Illustrative embodiments of the present invention provide a process for preparation of a polymorphic form APO-III of Rifaximin described herein wherein the drying is conducted at a temperature of from about 40° C. to about 70° C.

Illustrative embodiments of the present invention provide a process for preparation of a polymorphic form APO-III of Rifaximin described herein wherein the water content is about 1.5%.

Illustrative embodiments of the present invention provide the polymorphic form APO-IV of Rifaximin.

Illustrative embodiments of the present invention provide the polymorphic form APO-IV of Rifaximin described herein characterized by a PXRD diffractogram comprising peaks, in terms of degrees 2-theta, at approximately 7.1, 8.3, 8.6, 12.0, 12.9, 13.1, 13.4, 14.4, 15.7, 16.3, 19.1, 19.5, 19.7, 25.3 and 26.2.

Illustrative embodiments of the present invention provide the polymorphic form APO-IV of Rifaximin described herein characterized by a PXRD diffractogram comprising peaks, in terms of degrees 2-theta, at approximately 7.1, 8.3, 8.6, 12.0, 13.4, 16.3, 19.7 and 26.2.

Illustrative embodiments of the present invention provide the polymorphic form APO-IV of Rifaximin described herein characterized by a PXRD diffractogram substantially similar to the PXRD diffractogram as depicted in FIG. 7.

Illustrative embodiments of the present invention provide the polymorphic form APO-IV of Rifaximin described herein characterized by a PXRD diffractogram as depicted in FIG. 7.

Illustrative embodiments of the present invention provide a process for preparation of a polymorphic form APO-IV of Rifaximin, the process comprising:
  i. displacing a second organic solvent with water from a polymorphic form APO-II of Rifaximin to produce a damp cake; and
  ii. drying the damp cake until a water content of less than or equal to about 1.0% is reached.

Illustrative embodiments of the present invention provide a process for preparation of a polymorphic form APO-IV of Rifaximin described herein wherein the second organic solvent is selected from the group consisting of ethyl acetate, dichloromethane, isopropanol, n-butanol, acetonitrile, heptanes and mixtures thereof.

Illustrative embodiments of the present invention provide a process for preparation of a polymorphic form APO-IV of Rifaximin described herein wherein the second organic solvent is ethyl acetate.

Illustrative embodiments of the present invention provide a process for preparation of a polymorphic form APO-IV of Rifaximin described herein wherein the displacing a second organic solvent with water is performed by washing a polymorphic form APO-II of Rifaximin with water.

Illustrative embodiments of the present invention provide a process for preparation of a polymorphic form APO-IV of Rifaximin described herein wherein the displacing second organic solvent with water is performed by suspending or pulping a polymorphic form APO-II of Rifaximin in water.

Illustrative embodiments of the present invention provide a process for preparation of a polymorphic form APO-IV of Rifaximin described herein wherein the damp cake has a water content of from about 20% to about 50%.

Illustrative embodiments of the present invention provide a process for preparation of a polymorphic form APO-IV of Rifaximin described herein wherein the drying is conducted under vacuum or using a fluid bed dryer.

Illustrative embodiments of the present invention provide a process for preparation of a polymorphic form APO-IV of Rifaximin described herein wherein the drying is conducted at a temperature of from about 40° C. to about 70° C.

Illustrative embodiments of the present invention provide a process for preparation of a polymorphic form APO-IV of Rifaximin described herein wherein the water content is about 1%.

Illustrative embodiments of the present invention provide a process for the preparation of a polymorphic form APO-I of Rifaximin, the process comprising exposing polymorphic form APO-III, APO-IV or mixtures thereof to humidity.

Illustrative embodiments of the present invention provide a process for the preparation of a polymorphic form APO-I of Rifaximin described herein wherein the APO-III, APO-IV or mixtures thereof are exposed to humidity until the water content of the solid is from about 4.5% to about 8%.

Illustrative embodiments of the present invention provide a process for the preparation of a polymorphic form APO-I of Rifaximin described herein wherein the exposing a polymorphic form APO-III, APO-IV or mixtures thereof to humidity comprises contacting APO-III, APO-IV or mixtures thereof with a combination of water vapour and an inert gas.

Illustrative embodiments of the present invention provide a process for the preparation of the polymorphic form APO-I of Rifaximin described herein characterized by a PXRD diffractogram comprising peaks, in terms of degrees 2-theta, at approximately 6.7, 7.7, 8.4, 9.6, 12.7, 16.0, 16.7, 18.7 and 24.9.

Illustrative embodiments of the present invention provide a process for the preparation of the polymorphic form APO-I of Rifaximin described herein characterized by a PXRD diffractogram comprising peaks, in terms of degrees 2-theta, at approximately 6.7, 7.7, 8.4, 9.6, 12.7, 16.0 and 18.7.

Illustrative embodiments of the present invention provide a process for the preparation of the polymorphic form APO-I of Rifaximin described herein characterized by a PXRD diffractogram substantially similar to the PXRD diffractogram as depicted in FIG. 1.

Illustrative embodiments of the present invention provide a process for the preparation of the polymorphic form APO-I of Rifaximin described herein characterized by a PXRD diffractogram as depicted in FIG. 1.

Illustrative embodiments of the present invention provide a process for the preparation of the polymorphic form APO-I of Rifaximin described herein characterized by a 1% KBr FTIR spectrum comprising peaks, in terms of $cm^{-1}$, at approximately 3432, 2969, 2934, 1712, 1648, 1588, 1509, 1373, 1339, 1227, 1158, and 1124.

Illustrative embodiments of the present invention provide a process for preparation of the polymorphic form APO-I of Rifaximin described herein characterized by a 1% KBr FTIR spectrum comprising peaks, in terms of $cm^{-1}$, at approximately 2969, 2934, 1712, 1509, and 1124.

Illustrative embodiments of the present invention provide a process for the preparation of the polymorphic form APO-I of Rifaximin described herein characterized by a FTIR spectrum substantially similar to the FTIR spectrum as depicted in FIG. 2.

Illustrative embodiments of the present invention provide a process for the preparation of the polymorphic form APO-I of Rifaximin described herein characterized by a FTIR spectrum as depicted in FIG. 2.

In an illustrative embodiment, the present invention provides a process for preparation of the polymorphic form APO-II of Rifaximin, the process comprising:
  i. preparing a solution comprising Rifaximin, water and a third organic solvent wherein the solution has a water content of from about 0.5% to about 5%; and
  ii. crystallizing polymorphic form APO-II of Rifaximin.

Illustrative embodiments of the present invention provide a process for the preparation of a polymorphic form APO-II of Rifaximin described herein wherein the third organic solvent is selected from the group consisting of alcohols, alkyl ethers, alkyl esters, ketones, aromatic hydrocarbons, aliphatic hydrocarbons, halogenated hydrocarbons, and mixtures thereof.

Illustrative embodiments of the present invention provide a process for the preparation of the polymorphic form APO-II of Rifaximin described herein wherein the third organic solvent is selected from the group consisting of methanol, ethanol, propanol, isopropanol, butanol, methyl t-butyl ether, ethyl acetate, butyl acetate, acetone, methyl ethyl ketone, methyl isobutyl ketone, hexanes, heptanes, dichloromethane and mixtures thereof.

Illustrative embodiments of the present invention provide a process for the preparation of the polymorphic form APO-II of Rifaximin described herein wherein the third organic solvent is ethyl acetate.

Illustrative embodiments of the present invention provide a process for the preparation of the polymorphic form APO-II of Rifaximin described herein wherein the water content is from about 1% to about 3%.

Illustrative embodiments of the present invention provide a process for the preparation of the polymorphic form APO-II of Rifaximin described herein wherein the water content is from about 2.1% to about 2.7%.

Illustrative embodiments of the present invention provide a process for the preparation of the polymorphic form APO-II of Rifaximin described herein characterized by a PXRD diffractogram comprising peaks, in terms of degrees 2-theta, at approximately 6.4, 7.0, 7.3, 7.7, 9.0, 11.1, 14.5, 18.1, 19.6, 20.0, 20.8, and 26.7.

Illustrative embodiments of the present invention provide a process for the preparation of the polymorphic form APO-II of Rifaximin described herein characterized by a PXRD diffractogram comprising peaks, in terms of degrees 2-theta, at approximately 6.4, 7.0, 7.3, 7.7, 9.0, 11.1, 19.6 and 20.8.

Illustrative embodiments of the present invention provide a process for the preparation of the polymorphic form APO-II of Rifaximin described herein characterized by a PXRD diffractogram substantially similar to the PXRD diffractogram as depicted in FIG. 3.

Illustrative embodiments of the present invention provide a process for the preparation of the polymorphic form APO-II of Rifaximin described herein characterized by a PXRD diffractogram as depicted in FIG. 3.

Illustrative embodiments of the present invention provide a process for the preparation of the polymorphic form APO-II of Rifaximin described herein characterized by a 1% KBr FTIR spectrum comprising peaks, in terms of $cm^{-1}$, at approximately 3434, 2971, 2935, 1648, 1590, 1509, 1374, 1321, 1239, and 1120.

Illustrative embodiments of the present invention provide a process for the preparation of the polymorphic form APO-II of Rifaximin described herein characterized by a 1% KBr FTIR spectrum comprising peaks, in terms of $cm^{-1}$, at approximately 2971, 1509, and 1120.

Illustrative embodiments of the present invention provide a process for the preparation of the polymorphic form APO-II of Rifaximin described herein characterized by a FTIR spectrum substantially similar to the FTIR spectrum as depicted in FIG. 4.

Illustrative embodiments of the present invention provide a process for the preparation of the polymorphic form APO-II of Rifaximin described herein characterized by a FTIR spectrum as depicted in FIG. 4.

APO-I and APO-II polymorphic forms may have properties suitable for commercial use. These may include properties such as chemical stability, polymorphic stability, and/or varying solubilities relative to other forms of Rifaximin. APO-III and APO-IV are metastable forms which are useful as intermediates in the production of the APO-I polymorphic form from the APO-II polymorphic form.

Other aspects and features of the present invention will become apparent to those ordinarily skilled in the art upon review of the following description of specific embodiments of the invention with the accompanying Figures.

BRIEF DESCRIPTION OF THE DRAWINGS

Drawings which illustrate embodiments of the invention are.

DETAILED DESCRIPTION

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram, spectrum and/or data presented in a graph, but will nevertheless be known to a person of skill in the art.

When used in reference to a peak in a PXRD diffractogram, the term "approximately" means that the peak may vary by ±0.2 degrees 2-theta of the subject value.

When used in reference to a peak in a FTIR spectrum, the term "approximately" means that the peak may vary by ±5 $cm^{-1}$ of the subject value.

As used herein the term "water content" is reported as a percentage w/w. For example, the water content reported for a solution is weight water/weight total reaction mixture. The water content was measured using Karl Fischer (KF) titration.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 1% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

Figure 1:
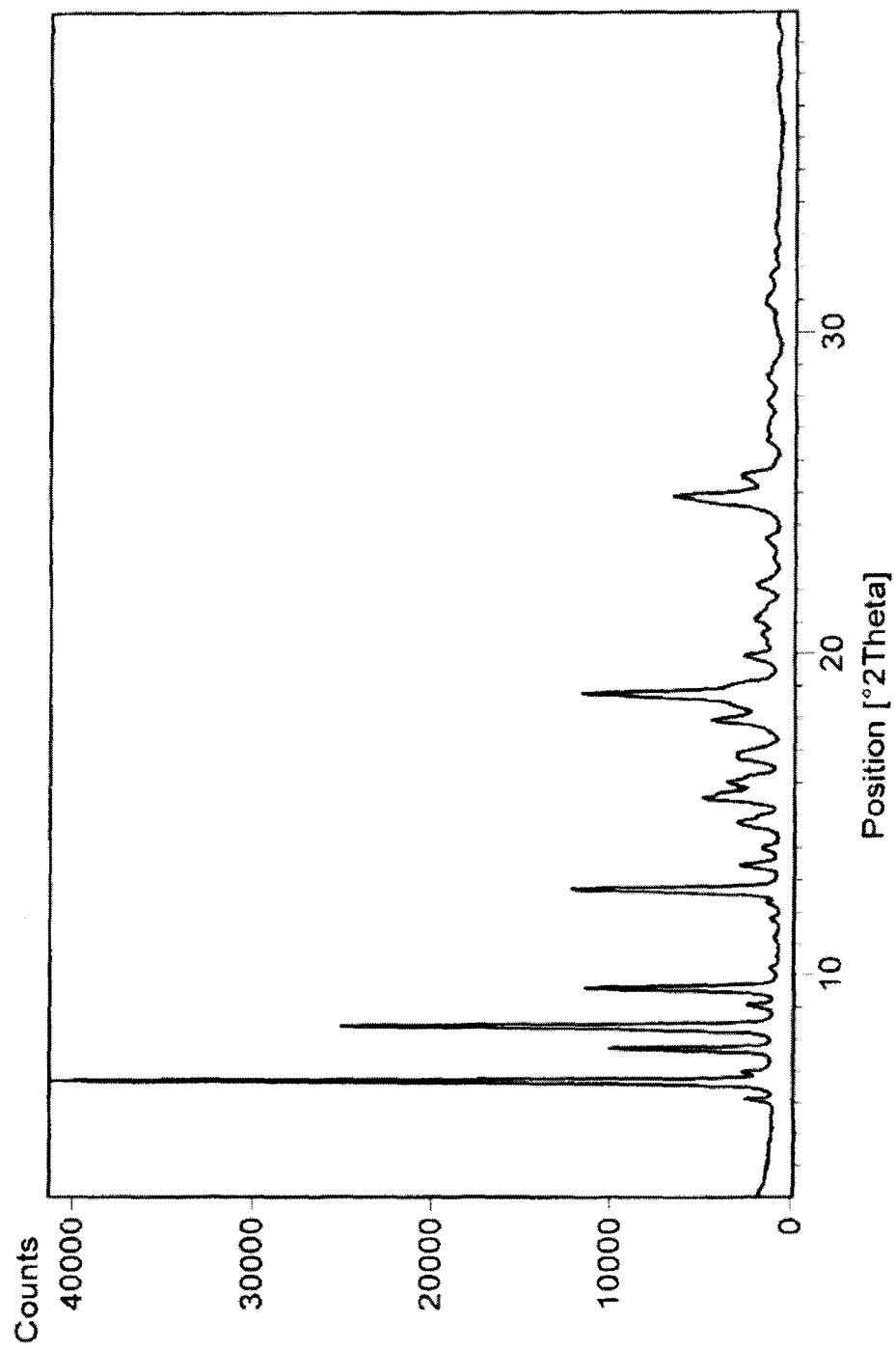
FIG. 1: is a powder X-ray diffraction (PXRD) diffractogram of APO-I

In an illustrative embodiment, the present invention comprises a process for the preparation of crystalline form of Rifaximin which is referred to herein as APO-I. APO-I may be characterized by an X-ray powder diffraction pattern comprising peaks, in terms of 2-theta, at approximately 6.7±0.2, 7.7±0.2, 8.4±0.2, 9.6±0.2, 12.7±0.2, 16.0±0.2, 16.7±0.2, 18.7±0.2 and 24.9±0.2. An illustrative PXRD diffractogram of APO-I is given in FIG. 1.

APO-I may have a reflection ("peak") at any one or more of the values expressed in degrees 2-theta given in Table 1. Although values are given in the tables below, APO-I may be defined by the claimed peaks and a particular claim may be limited to one peak only, or several peaks. The form APO-I does not have to include all or even many of the peaks listed in Table 1. Some illustrative and non-limiting possible observations regarding relative intensities of the peaks are set out in Table 1.

TABLE 1

Relative peak intensities for APO-I

| Angle 2-theta | Relative intensity % |
| --- | --- |
| 6.69 | 100.00 |
| 6.96 | 4.22 |
| 7.70 | 22.88 |
| 8.40 | 60.93 |
| 9.07 | 4.08 |
| 9.59 | 27.42 |
| 12.68 | 29.40 |
| 13.43 | 5.24 |
| 13.96 | 2.23 |
| 14.64 | 4.41 |
| 15.47 | 9.98 |
| 16.02 | 6.79 |
| 16.72 | 5.26 |
| 17.94 | 7.24 |
| 18.72 | 24.38 |
| 19.90 | 4.67 |
| 24.90 | 14.31 |
| 25.48 | 5.49 |

Figure 2:
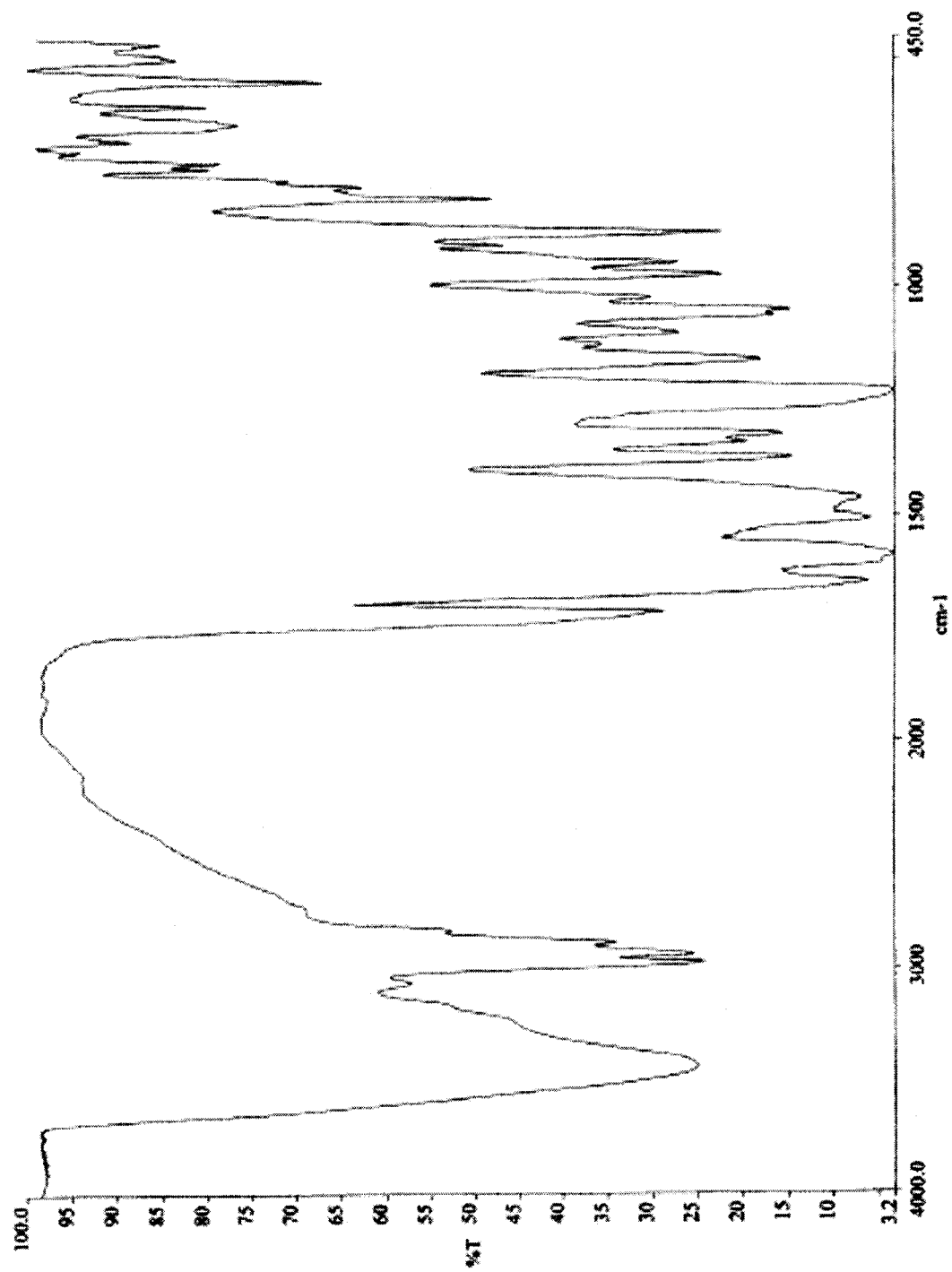
FIG. 2: is a Fourier Transform Infrared (FTIR) spectrum of APO-I

In an illustrative embodiment, the present invention comprises a process for the preparation of crystalline form of Rifaximin which is referred to herein as APO-I. APO-I may be characterized by an FTIR spectrum comprising absorption bands, expressed in $cm^{-1}$, at approximately 3432, 2969, 2934, 1712, 1648, 1588, 1509, 1373, 1339, 1227, 1158, and 1124. An illustrative FTIR spectrum of APO-I is given in FIG. 2.

APO-I Rifaximin may have an absorption band ("peak") at any one or more of the values expressed in $cm^{-1}$ given in Table 2. Some illustrative and non limiting possible observations regarding peak intensity (% transmission) of the peaks are also set out in Table 2.

TABLE 2

Form APO-I Rifaximin

| Peak ($cm^{-1}$) | Intensity (% Transmission) |
| --- | --- |
| 3432.6 | 24.95 |
| 2969.5 | 24.12 |
| 2934.5 | 25.30 |
| 1712.3 | 28.63 |
| 1647.7 | 6.05 |
| 1588.0 | 3.16 |

TABLE 2-continued

Form APO-I Rifaximin

| Peak (cm$^{-1}$) | Intensity (% Transmission) |
|---|---|
| 1509.1 | 5.72 |
| 1373.1 | 14.44 |
| 1339.1 | 19.37 |
| 1227.4 | 3.23 |
| 1158.3 | 17.95 |
| 1124.1 | 35.66 |

In an illustrative embodiment, the present invention provides a process for the preparation of a polymorphic form APO-I of Rifaximin described herein wherein the APO-III, APO-IV or mixtures thereof are exposed to humidity until the water content of the solid is from about 4.5% to about 8%.

The APO-III, APO-IV or mixtures thereof may be exposed to humidity under various conditions. The polymorphic form(s) may be placed in a closed chamber of fixed humidity until the desired water content is attained. Alternatively, a dynamic process may be used wherein the exposure comprises contacting the polymorphic form(s) with a stream of water vapour and an inert gas.

The exposing APO-III, APO-IV or mixtures thereof to humidity may be performed at a suitable temperature. In an embodiment, the temperature may be from about room temperature to about 60° C.

Figure 3:
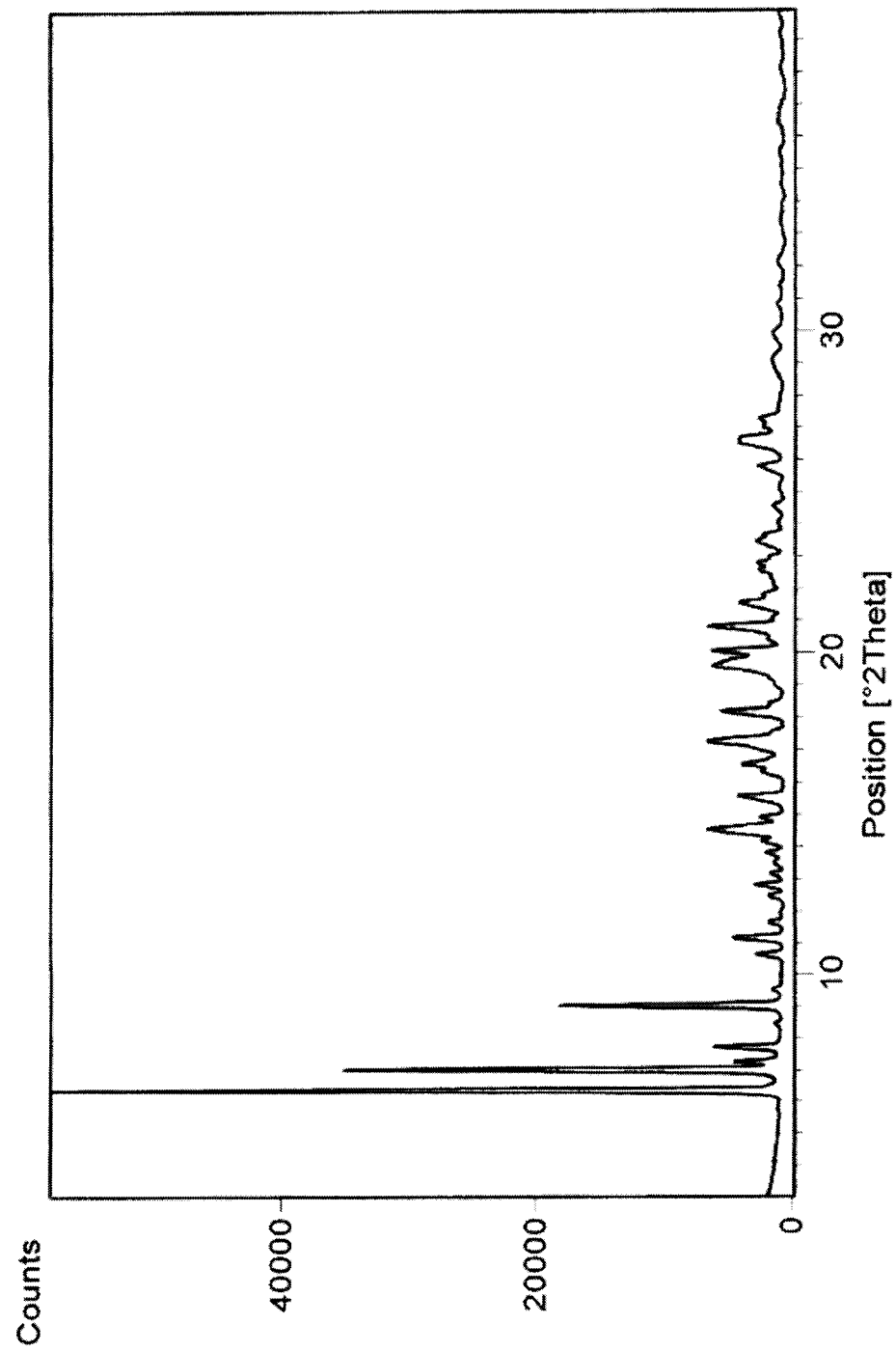
FIG. 3: is a powder X-ray diffraction (PXRD) diffractogram of APO-II

In an illustrative embodiment, the present invention comprises a process for the preparation of a crystalline form of Rifaximin which is referred to herein as APO-iI. APO-II may be characterized by an X-ray powder diffraction pattern comprising peaks, in terms of 2-theta, at approximately 6.4±0.2, 7.0±0.2, 7.3±0.2, 7.7±0.2, 9.0±0.2, 11.1±0.2, 14.5±0.2, 18.1±0.2, 19.6±0.2, 20.0±0.2, 20.8±0.2, and 26.7±0.2. An illustrative PXRD diffractogram of APO-II is given in FIG. 3.

APO-II may have a reflection ("peak") at any one or more of the values expressed in degrees 2-theta given in Table 3. Although values are given in the tables below, APO-II may be defined by the claimed peaks and a particular claim may be limited to one peak only, or several peaks. The form APO-II does not have to include all or even many of the peaks listed in Table 3. Some illustrative and non-limiting possible observations regarding relative intensities of the peaks are set out in Table 3.

TABLE 3

Relative peak intensities for APO-II

| Angle 2-theta | Relative intensity % |
|---|---|
| 6.39 | 100.00 |
| 7.05 | 60.76 |
| 7.30 | 6.11 |
| 7.74 | 9.10 |
| 9.05 | 30.63 |
| 10.62 | 3.45 |
| 11.15 | 6.85 |
| 12.45 | 1.95 |
| 12.80 | 3.55 |
| 13.80 | 2.14 |
| 14.15 | 2.76 |
| 14.54 | 10.04 |
| 14.89 | 2.97 |
| 15.56 | 6.15 |
| 16.55 | 5.05 |
| 18.15 | 8.14 |
| 19.57 | 8.87 |
| 20.04 | 9.73 |
| 20.78 | 9.60 |

TABLE 3-continued

Relative peak intensities for APO-II

| Angle 2-theta | Relative intensity % |
|---|---|
| 21.52 | 5.75 |
| 26.66 | 6.01 |

Figure 4:
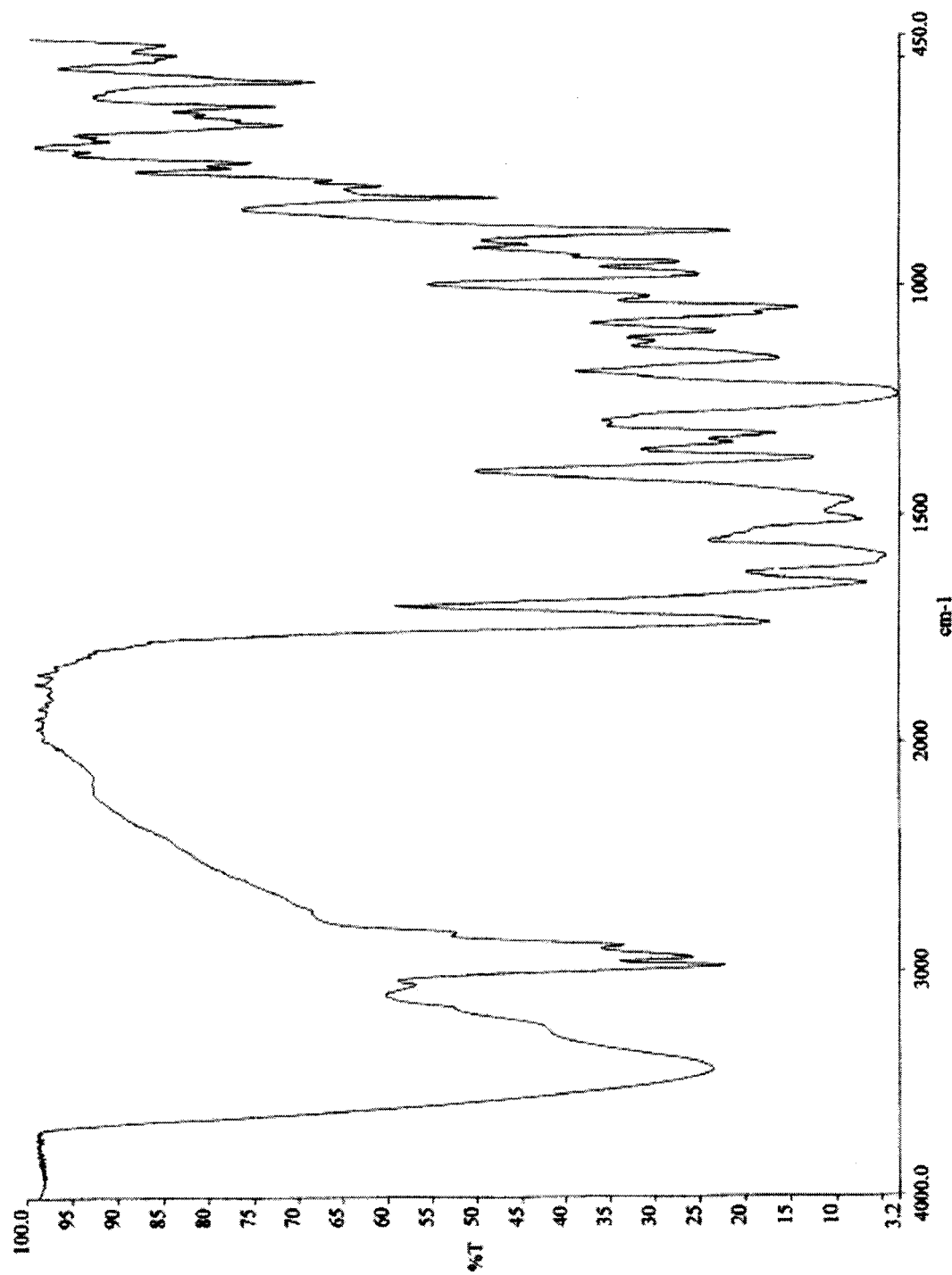
FIG. 4: is a Fourier Transform Infrared (FTIR) spectrum of APO-II

In an illustrative embodiment, the present invention comprises a process for the preparation of crystalline form of Rifaximin which is referred to herein as APO-II. APO-II may be characterized by an FTIR spectrum comprising absorption bands, expressed in cm$^{-1}$, at approximately 3434, 2971, 2935, 1648, 1590, 1509, 1374, 1321, 1239, and 1120. An illustrative FTIR spectrum of APO-11 is given in FIG. 4.

APO-II Rifaximin may have an absorption band ("peak") at any one or more of the values expressed in cm$^{-1}$ given in Table 4. Some illustrative and non limiting possible observations regarding peak intensity (% transmission) of the peaks are also set out in Table 4.

TABLE 4

Form APO-II Rifaximin

| Peak (cm$^{-1}$) | Intensity (% Transmission) |
|---|---|
| 3433.7 | 23.47 |
| 2971.4 | 22.25 |
| 2935.0 | 25.76 |
| 1648.3 | 6.64 |
| 1589.7 | 4.57 |
| 1509.1 | 7.14 |
| 1373.8 | 12.51 |
| 1321.3 | 16.57 |
| 1119.5 | 29.96 |

In an illustrative embodiment, the present invention provides a process for preparation of the polymorphic form APO-II of Rifaximin, the process comprising:

i. preparing a solution comprising Rifaximin, water and a third organic solvent wherein the solution has a water content of from about 0.5% to about 5%; and ii. crystallizing polymorphic form APO-II of Rifaximin.

The third organic solvent may be selected from the group consisting of alcohols (e.g. methanol, ethanol, propanol, isopropanol, and butanol), alkyl ethers (e.g. tetrahydrofuran, dioxane, diethyl ether, and methyl t-butyl ether), alkyl esters (e.g. ethyl acetate, and isopropyl acetate), ketones (e.g. acetone, methyl ethyl ketone, and methyl isobutyl ketone), aromatic hydrocarbons (e.g. toluene), aliphatic hydrocarbons (e.g. hexanes, and heptanes), nitriles (e.g. acetonitrile), halogenated hydrocarbons (e.g. dichloromethane and dichloroethane), and mixtures thereof. In some embodiments, the third organic solvent is selected from the group consisting of ethyl acetate, dichloromethane, isopropanol, n-butanol, acetonitrile, heptanes and mixtures thereof. In a preferred embodiment, the third organic solvent is ethyl acetate.

The water content of the solution may vary from about 0.5% to about 5%. The optimal range may vary depending on the solvent system employed. In an embodiment, the water content of the solution may be from about 1% to about 3%. In an embodiment, the optimal range for ethyl acetate may be from about 2.1% to about 2.7%. A water content near the upper limit of 5% may be suitable in some solvent systems but may result in production of undesired polymorphic forms compared to other solvent systems.

In the preparation of a solution comprising Rifaximin, water and a third organic solvent, the water may be derived from any source, including from the starting materials, solvents and/or from explicit addition of water.

The preparation of a solution comprising Rifaximin, water and a third organic solvent may be conducted at a temperature of from about room temperature to about the boiling point of the solvent. In an embodiment, the temperature is from about 30° C. to about 65° C.

The crystallization of polymorphic form APO-II of Rifaximin may be conducted by cooling the solution comprising Rifaximin, water to a suitable temperature. In an embodiment, the solution may be cooled to a temperature of from about room temperature to about 35° C. The crystallization may be induced by seeding.

In an illustrative embodiment, the present invention comprises a crystalline form of Rifaximin which is referred to herein as APO-III. APO-III may be characterized by an X-ray powder diffraction pattern comprising peaks, in terms of 2-theta, at approximately 7.1±0.2, 8.4±0.2, 9.1±0.2, 11.6±0.2, 13.1±0.2, 15.3±0.2, 16.4±0.2, 18.5±0.2, 18.8±0.2, 19.4±0.2 and 25.0±0.2. An illustrative PXRD diffractogram of APO-III is given in FIG. 5.

APO-III may have a reflection ("peak") at any one or more of the values expressed in degrees 2-theta given in Table 5. Although values are given in the tables below, APO-III may be defined by the claimed peaks and a particular claim may be limited to one peak only, or several peaks. The form APO-III does not have to include all or even many of the peaks listed in Table 5. Some illustrative and non-limiting possible observations regarding relative intensities of the peaks are set out in Table 5.

TABLE 5

Relative peak intensities for APO-III

| Angle 2-theta | Relative intensity % |
|---|---|
| 7.08 | 100.00 |
| 8.39 | 96.27 |
| 9.10 | 32.51 |
| 11.59 | 7.80 |
| 12.30 | 6.63 |
| 12.86 | 21.03 |
| 13.11 | 32.12 |
| 14.21 | 13.09 |
| 14.47 | 7.15 |
| 15.32 | 21.92 |
| 15.72 | 18.99 |
| 16.45 | 24.77 |
| 17.17 | 13.50 |
| 18.48 | 26.48 |
| 18.85 | 30.38 |
| 19.37 | 25.08 |
| 20.93 | 8.40 |
| 24.98 | 22.68 |

Figure 6:
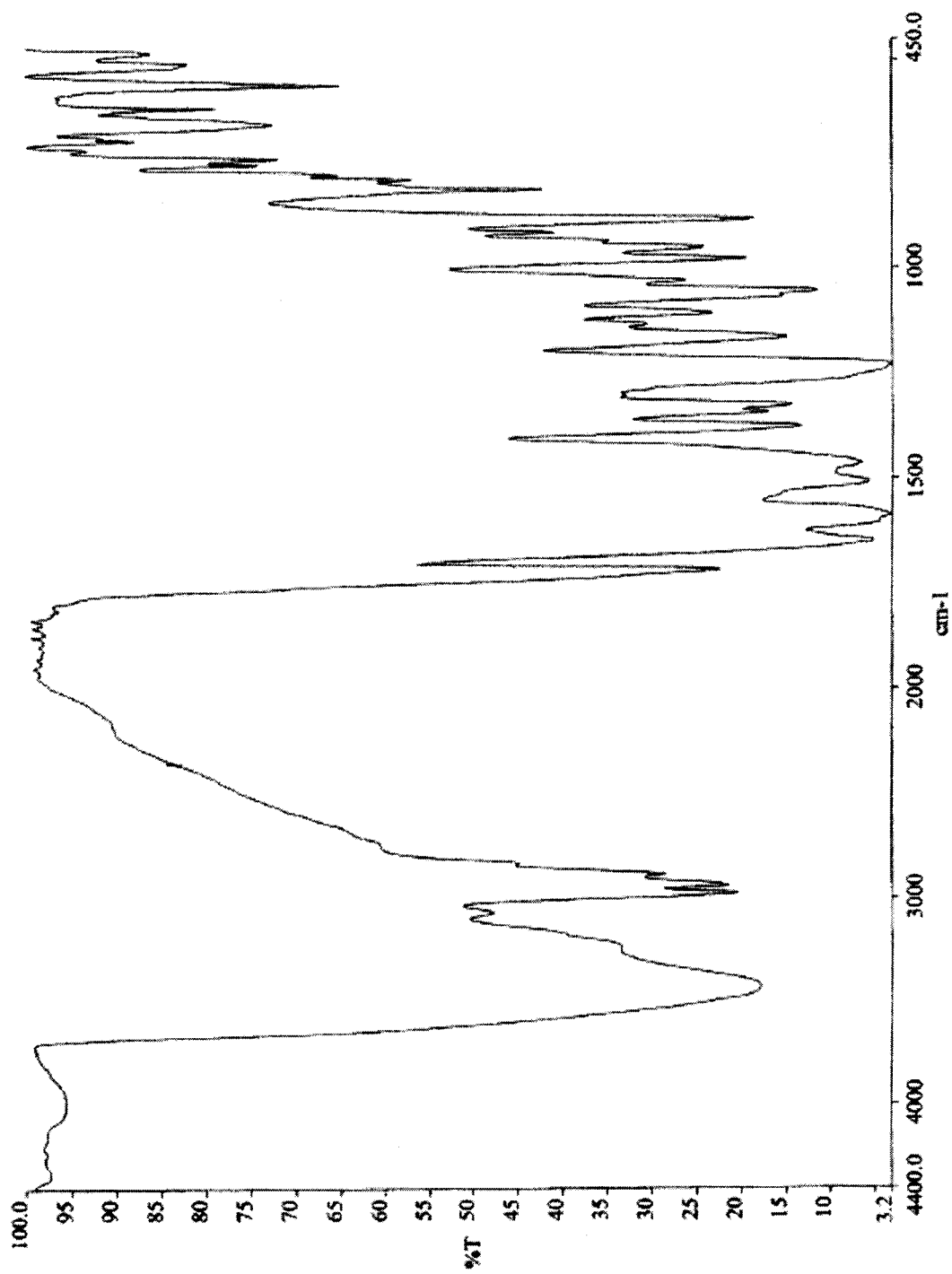
FIG. 6: is a Fourier Transform Infrared (FTIR) spectrum of APO-III

In an illustrative embodiment, the present invention comprises a process for the preparation of crystalline form of Rifaximin which is referred to herein as APO-III. APO-III may be characterized by an FTIR spectrum comprising absorption bands, expressed in cm$^{-1}$, at approximately 3427, 2968, 2934, 1714, 1648, 1588, 1506, 1373, 1338, 1226, 1158, and 1124. An illustrative FTIR spectrum of APO-III is given in FIG. 6.

APO-III Rifaximin may have an absorption band ("peak") at any one or more of the values expressed in cm$^{-1}$ given in Table 6. Some illustrative and non limiting possible observations regarding peak intensity (% transmission) of the peaks are also set out in Table 6.

TABLE 6

Form APO-III Rifaximin

| Peak (cm$^{-1}$) | Intensity (% Transmission) |
|---|---|
| 3426.7 | 17.80 |
| 2968.1 | 20.43 |
| 2933.8 | 21.53 |
| 1713.8 | 22.52 |
| 1648.2 | 5.26 |
| 1587.7 | 3.29 |
| 1506.0 | 5.65 |
| 1372.9 | 13.39 |
| 1338.0 | 17.11 |
| 1226.4 | 3.15 |
| 1157.5 | 15.06 |
| 1124.3 | 30.68 |

In an illustrative embodiment, the present invention provides a process for preparation of a polymorphic form APO-III of Rifaximin, the process comprising:
 i. displacing a first organic solvent with water from a polymorphic form APO-II of Rifaximin to produce a damp cake; and
 ii. drying the damp cake until a water content of between about 0.5% to about 2% is reached.

The first organic solvent may be displaced with water by any known method. For example, the first organic solvent may be displaced by washing the APO-III form with water or by suspending or pulping the APO-III form in water. Traces of the first organic solvent may not impact the process.

In many embodiments, the damp cake may have a water content of from about 20% to about 50%.

The drying may be conducted under ambient pressure or it may be conducted under vacuum. The drying may be conducted using a fluid bed dryer. The drying may be conducted at a suitable temperature whereby degradation of the compound does not occur. The drying may be conducted at an elevated temperature. The drying may be conducted at a temperature of from about 40° C. to about 70° C.

In an illustrative embodiment, the present invention comprises a crystalline form of Rifaximin which is referred to herein as APO-IV. APO-IV may be characterized by an X-ray powder diffraction pattern comprising peaks, in terms of 2-theta, at approximately 7.1±0.2, 8.3±0.2, 8.6±0.2, 12.0±0.2, 12.9±0.2, 13.1±0.2, 13.4±0.2, 14.4±0.2, 15.7±0.2, 16.3±0.2, 19.1±0.2, 19.5±0.2, 19.7±0.2, 25.3±0.2 and 26.2±0.2. An illustrative PXRD diffractogram of APO-IV is given in FIG. 7.

APO-IV may have a reflection ("peak") at any one or more of the values expressed in degrees 2-theta given in Table 7. Although values are given in the tables below, APO-IV may be defined by the claimed peaks and a particular claim may be limited to one peak only, or several peaks. The form APO-IV does not have to include all or even many of the peaks listed in Table 7. Some illustrative and non-limiting possible observations regarding relative intensities of the peaks are set out in Table 7.

TABLE 7

Relative peak intensities for APO-IV

| Angle 2-theta | Relative intensity % |
|---|---|
| 7.15 | 62.36 |
| 8.26 | 100.00 |
| 8.63 | 41.52 |
| 9.63 | 4.17 |

TABLE 7-continued

Relative peak intensities for APO-IV

| Angle 2-theta | Relative intensity % |
|---|---|
| 10.48 | 5.99 |
| 12.01 | 13.34 |
| 12.88 | 17.42 |
| 13.08 | 16.39 |
| 13.36 | 16.80 |
| 14.42 | 13.89 |
| 15.71 | 18.32 |
| 16.31 | 17.68 |
| 19.13 | 16.12 |
| 19.47 | 20.20 |
| 19.69 | 24.94 |
| 25.35 | 7.24 |
| 26.17 | 14.80 |

In an illustrative embodiment, the present invention provides a process for preparation of a polymorphic form APO-IV of Rifaximin, the process comprising:
  i. displacing a second organic solvent with water from a polymorphic form APO-II of Rifaximin to produce a damp cake; and
  ii. drying the damp cake until a water content of less than or equal to about 1.0% is reached.

The second organic solvent may be displaced with water by any known method. For example, the second organic solvent may be displaced by washing the APO-III form with water or by suspending or pulping the APO-III form in water. Traces of the second organic solvent may not impact the process.

In many embodiments, the damp cake may have a water content from about 20% to about 50%.

The drying may be conducted under ambient pressure or it may be conducted under vacuum. The drying may be conducted using a fluid bed dryer. The drying may be conducted at a suitable temperature whereby degradation of the compound does not occur. The drying may be conducted at an elevated temperature. The drying may be conducted at a temperature of from about 40° C. to about 70° C.

The following examples are illustrative of some of the embodiments of the invention described herein. These examples do not limit the spirit or scope of the invention in any way.

EXAMPLES

Powder X-Ray Diffraction Analysis: The data were acquired on a PANanalytical X-Pert Pro MPD diffractometer with fixed divergence slits and an X-Celerator RTMS detector. The diffractometer was configured in Bragg-Brentano geometry; data was collected over a 2-theta range of 3 to 40 using CuKα radiation at a power of 40 mA and 45 kV. CuKβ radiation was removed using a divergent beam nickel filter. A step size of 0.017 degrees was used. In the examples shown in FIGS. 1 and 3, a step time of 200 seconds, an incident beam soller slit of 0.01 rad and a diffracted beam soller slit of 0.02 rad was used.

Figure 5:
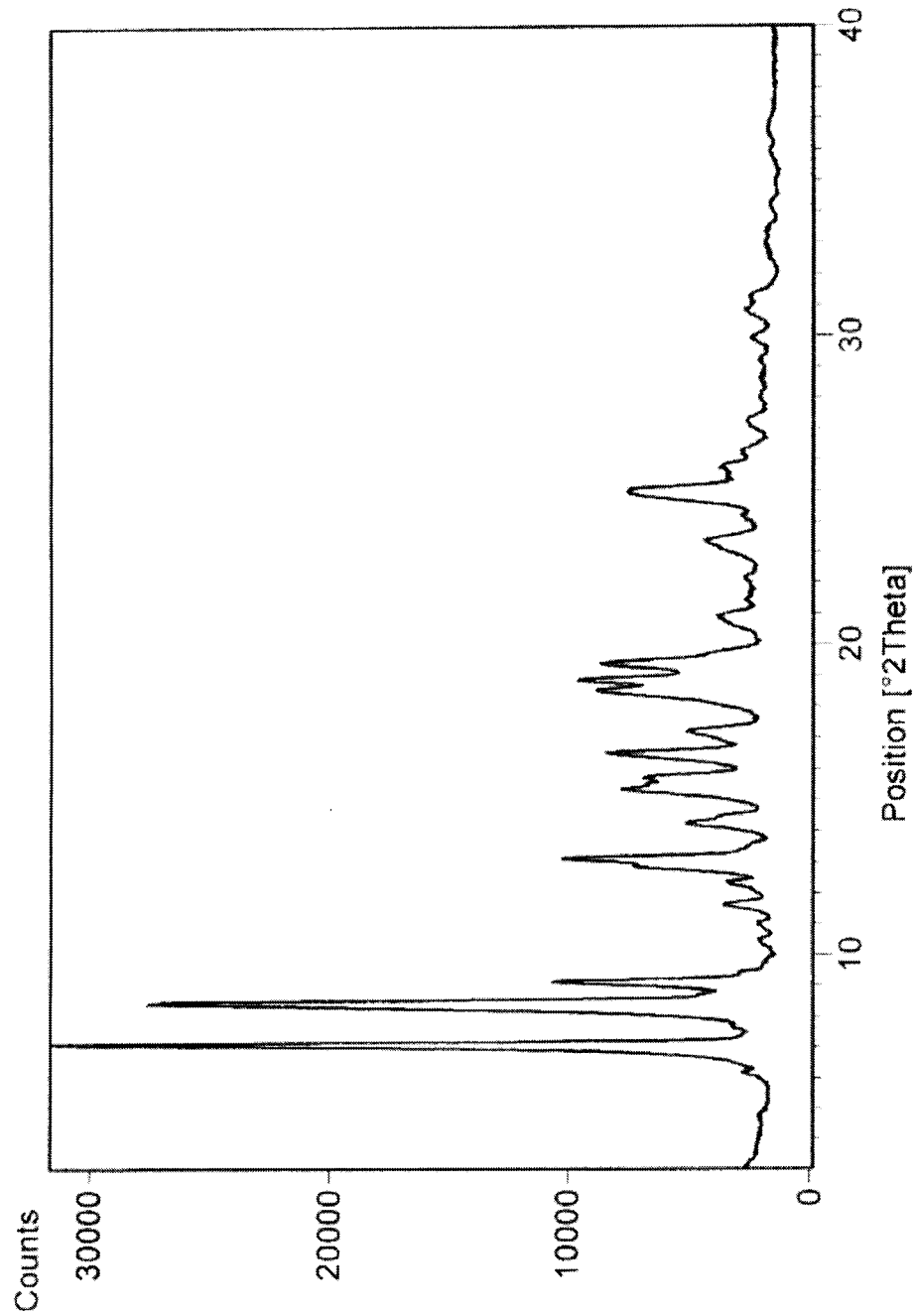
FIG. 5: is a powder X-ray diffraction (PXRD) diffractogram of APO-III
Figure 7:
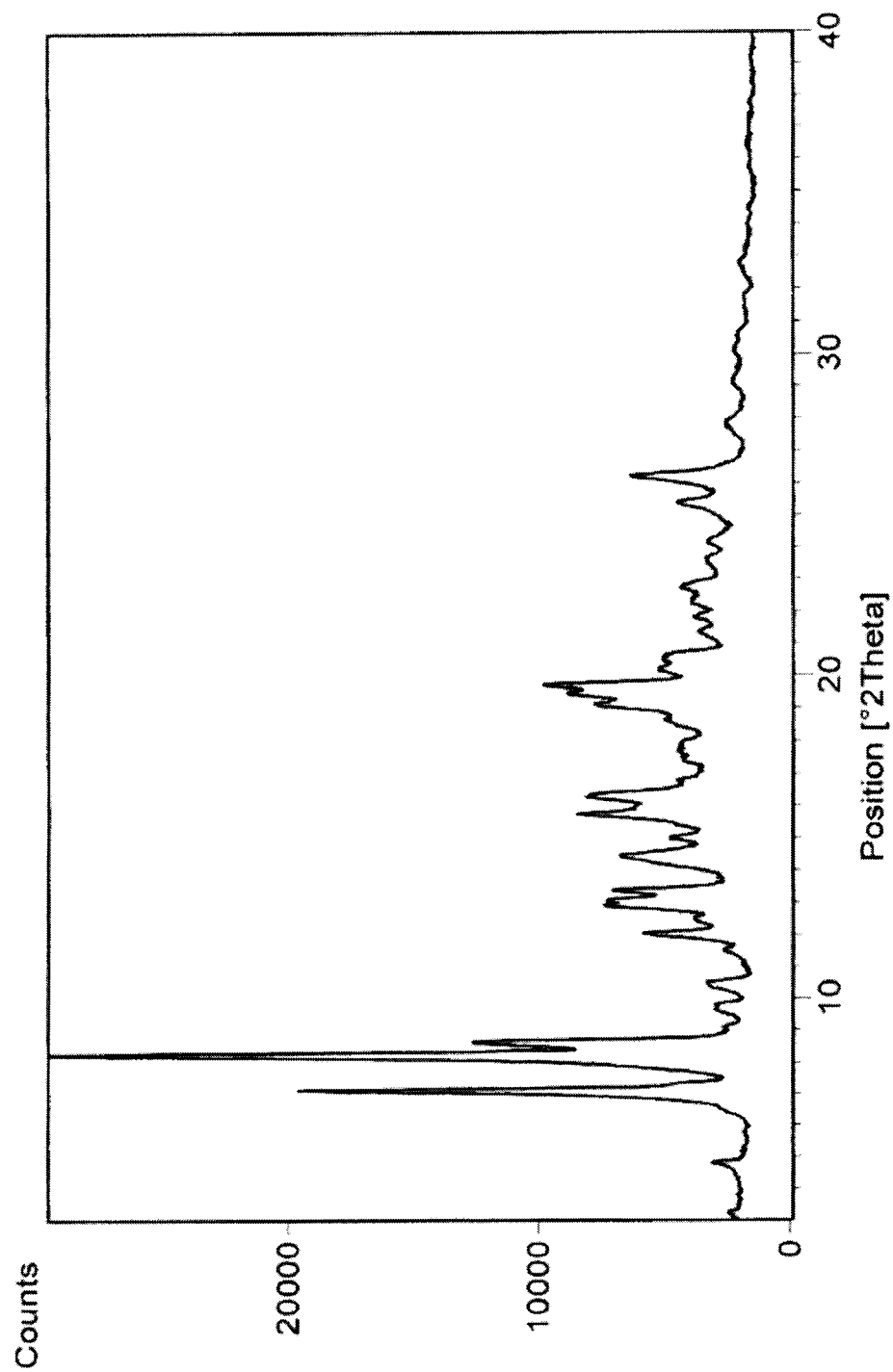
FIG. 7: is a powder X-ray diffraction (PXRD) diffractogram of APO-IV

In the examples shown in FIGS. 5 and 7, a step time of 20 seconds, an incident beam soller slit of 0.04 rad and a diffracted beam soller slit of 0.04 rad was used. Samples were rotated at 1 Hz to reduce preferred orientation effects. The samples were prepared by the back-loading technique.

Fourier Transform Infrared (FTIR) Analysis: The FTIR spectrum was collected at 4 cm$^{-1}$ resolution using a Perkin Elmer Paragon 1100 single beam FTIR instrument. The samples were intimately mixed in an approximately 1:100 ratio (w/w) with potassium bromide using an agate mortar and pestle to a fine consistency; the mixture was compressed in a pellet die at a pressure of 4 to 6 tonnes for a time period between 2 and 5 minutes. The resulting disk was scanned 4 times versus a collected background. Data was baseline corrected and normalized.

Example 1

Preparation of Forms APO-II Rifaximin

Rifaximin (10 g, KF=1.8%) was dissolved in ethyl acetate (30 mL) followed by adding this solution to a mixture of heptanes (50 mL) and water (1 mL) at 45-50° C. After stirring at 45-50° C. for 4 hrs, the resulting suspension was stirred at room temperature for 0.5 hrs. The suspension was filtered, washed with water (50 mL) and air dried at room temperature for 2 days to give Form APO-II Rifaximin (10.7 g).

Example 2

Preparation of Form APO-II Rifaximin

Rifaximin (100 g, KF=1.8%) was dissolved in ethyl acetate (300 mL) and water (5 mL) and heated to 40-45° C., followed by addition of heptanes (500 mL). After stirring at 40-45° C. for 6 hrs, the resulting slurry was stirred at room temperature for 13 hrs. The slurry was filtered, washed with water (400 mL) and suction dried at room temperature for 0.5 hrs to give Form APO-II Rifaximin (128.0 g).

Example 3

Preparation of Form APO-II Rifaximin

Rifaximin (300 g, KF=1.3%) was dissolved in ethyl acetate (900 mL) and water (15 mL) and heated to 40-45° C., followed by addition of heptanes (1500 mL) and Form APO-II seeds. After stirring at 40-45° C. for 8 hrs, the resulting slurry was stirred at room temperature for 13 hrs. The slurry was filtered, washed with heptanes (600 mL) and dried in a vacuum oven at 45-50° C. to afford Form APO-II Rifaximin (305.0 g).

Example 4

Preparation of Form APO-II Rifaximin

Rifaximin (100 g, KF=1.5%) was dissolved in ethyl acetate (300 mL) and water (5 mL) and heated to 40-45° C., followed by addition of heptanes (500 mL). After stirring at 40-45° C. for 5.5 hrs, the resulting slurry was stirred at room temperature for 13 hrs. The slurry was filtered, washed with heptanes (400 mL) and suction dried at room temperature for 0.5 hrs to provide Form APO-II Rifaximin (113.9 g).

Example 5

Preparation of Form APO-II Rifaximin

Rifaximin (10 g, KF=1.8%) was dissolved in ethyl acetate (30 mL) and water (0.7 mL) at room temperature. After stirring at room temperature for 23 hrs, the resulting suspension was filtered and air dried at room temperature for 16 hrs to provide Form APO-II Rifaximin (6.8 g).

Example 6

Preparation of Form APO-II Rifaximin

Rifaximin (50 g, KF=1.5%) was dissolved in ethyl acetate (150 mL) and water (2.0 mL) at room temperature, followed by addition of Form APO-II seeds. After stirring at room temperature for 41 hrs, the resulting slurry was cooled to 0-5° C. and stirred for 4 hrs. The slurry was filtered and dried in a vacuum oven at 45-50° C. to give Form APO-II Rifaximin (41.1 g).

Example 7

Preparation of Form APO-II Rifaximin

Rifaximin (70 g, KF=7.2%) was dissolved in ethyl acetate (210 mL) and water (2.0 mL) at 60-70° C. and then cooled to 30-35° C. Following addition of Form APO-II seeds, the solution was cooled to room temperature and stirred for 18 hrs. The resulting slurry was cooled to 0-5° C. and stirred for 3 hrs. The slurry was filtered, washed with heptanes (70 mL) and dried in a vacuum oven at 45-50° C. to afford Form APO-II Rifaximin (60.4 g).

Example 8

Preparation of Form APO-II Rifaximin

Rifaximin (100 g, KF=6.3%) was dissolved in ethyl acetate (300 mL) and water (1.1 mL) at 35-40° C., the solution was seeded with Form APO-II, and cooled to room temperature. After stirring for 37 hrs, the resulting slurry was filtered, washed with heptanes (100 mL) and dried in a vacuum oven at 55-60° C. to provide Form APO-II Rifaximin (77.3 g).

Example 9

Preparation of Form APO-II Rifaximin

Rifaximin (106 g, KF=5.6%) was dissolved in ethyl acetate (300 mL) and water (1.5 mL) at 35-40° C. (solution KF=2.0%), the solution was seeded with
Form APO-II, and cooled to room temperature. After stirring for 66 hrs, the resulting slurry was filtered and dried in a vacuum oven at 45-50° C. to give Form APO-II Rifaximin (91.2 g).

Example 10

Preparation of Form APO-II Rifaximin

Rifaximin (106 g, KF=5.6%) was dissolved in ethyl acetate (300 mL) and water (1.5 mL) at 35-40° C. (solution KF=2.1%), the solution was seeded with Form APO-II, and cooled to room temperature. After stirring for 17 hrs, the resulting slurry was cooled to 0-5° C. and stirred for 7 hrs. The slurry was filtered and dried in a vacuum oven at 45-50° C. to provide Form APO-II Rifaximin (96.7 g).

Example 11

Preparation of Form APO-II Rifaximin

Rifaximin (123 g, KF=3.9%) was dissolved in ethyl acetate (354 mL) and water (4.2 mL) at 65-70° C. (solution KF=2.1%) and then cooled to 40-45° C.
Following addition of Form APO-II seeds, the solution was cooled to room temperature and stirred for 13 hrs. The resulting slurry was cooled to 0-5° C. and stirred for 7 hrs. The slurry was filtered and dried in a vacuum oven at 45-50° C. to afford Form APO-II Rifaximin (111.3 g).

Example 12

Preparation of Form APO-II Rifaximin

Rifaximin (50 g, KF=1.3%) was dissolved in ethyl acetate (150 mL) and water (4.0 mL) at 40-45° C. (solution KF=2.8%) and then cooled to 35-40° C. Form APO-II seeds were added, and the solution was cooled to room temperature and stirred for 20 hrs. The resulting slurry was cooled to 0-5° C. and stirred for 7 hrs.

The slurry was filtered and dried in a vacuum oven at 45-50° C. affording Form APO-II Rifaximin (45.8 g).

Example 13

Preparation of Form APO-II Rifaximin

Rifaximin (50 g, KF=1.3%) was dissolved in ethyl acetate (150 mL) and water (2.0 mL) at 35-40° C. (solution KF=1.5%), the solution was seeded with Form APO-II, and cooled to room temperature. After stirring for 19 hrs, the resulting slurry was cooled to 0-5° C. and stirred for 7 hrs. The slurry was filtered and air dried at room temperature for 15 hrs to give Form APO-II Rifaximin (26.9 g).

Example 14

Preparation of Form APO-II Rifaximin

Rifaximin (300 g, KF=0.7%) was dissolved in ethyl acetate (600 mL) and water (20 mL) at 50-55° C. (solution KF=2.5%) and then cooled to 35-40° C. Following addition of Form APO-II seeds, the solution was cooled to room temperature and stirred for 19 hrs. The resulting slurry was cooled to 0-5° C. and stirred for 7 hrs. The slurry was filtered and dried in a vacuum oven at 45-50° C. providing Form APO-II Rifaximin (298.4 g).

Example 15

Preparation of Form APO-II Rifaximin

Rifaximin (20 g, KF=0.7%) was dissolved in ethyl acetate (40 mL) and water (1.2 mL) at 55-60° C. (solution KF=2.2%) and then cooled to 35-40° C. Form APO-II seeds were added, and the solution was stirred at 35° C. for 17 hrs. The resulting slurry was filtered and dried in a vacuum oven at 45-50° C. affording Form APO-II Rifaximin (17.9 g).

Example 16

Preparation of Form APO-II Rifaximin

Rifaximin (5.0 g, KF=1.5%) was dissolved in n-butanol (25 mL) and water (1.0 mL) with slight heating, and the solution was seeded with Form APO-II. The solution was cooled to room temperature and stirred for 20 hrs. The resulting slurry was filtered, washed with heptanes (10 mL) and suction dried at room temperature for 15 min to give Form APO-II Rifaximin (1.6 g).

Example 17

Preparation of Form APO-II Rifaximin

Rifaximin (7.0 g, KF=0.5%) was dissolved in n-butanol (35 mL) and water (1.0 mL) at 75-80° C. and then cooled to room temperature. Following addition of Form APO-II seeds, the solution was stirred at room temperature for 44 hrs. The resulting slurry was filtered and dried in a vacuum oven at 45-50° C. affording Form APO-II Rifaximin (3.5 g).

Example 18

Preparation of Form APO-II Rifaximin

Rifaximin (5.0 g, KF=1.3%) was dissolved in dichloromethane (25 mL) at room temperature, followed by addition of heptanes (25 mL) and water (0.5 mL). The solution was cooled to 0-5° C., seeded with Form APO-II and stirred for 4 hrs. The resulting slurry was filtered, washed with heptanes (15 mL) and suction dried at room temperature for 10 min to give Form APO-II Rifaximin (2.7 g).

Example 19

Preparation of Form APO-II Rifaximin

Rifaximin (5.0 g, KF=1.3%) was dissolved in dichloromethane (25 mL) at reflux temperature, followed by addition of water (0.5 mL), heptanes (25 mL) and Form APO-II seeds. After 2 hrs at reflux, the resulting slurry was filtered, washed with heptanes (15 mL) and suction dried at room temperature for 10 min to give Form APO-II Rifaximin (4.8 g).

Example 20

Preparation of Form APO-II Rifaximin

Rifaximin (5.0 g, KF=15.4%) was dissolved in isopropanol (25 mL) at 50-55° C., followed by addition of heptanes (25 mL) and Form APO-II seeds. After stirring at 50-55° C. for 1 hr, the mixture was cooled to 40-45° C. and heptanes (25 mL) was added. The resulting slurry was stirred at 40-45° C. for 2 hrs and then at room temperature for 16 hrs. The slurry was filtered, washed with heptanes (15 mL) and dried in a vacuum oven at 55-60° C. affording Form APO-II Rifaximin (4.0 g).

Example 21

Preparation of Form APO-II Rifaximin

Rifaximin (10 g, KF=1.3%) was dissolved in isopropanol (50 mL) and water (1.8 mL) at 50-55° C., followed by addition of heptanes (100 mL) and Form APO-II seeds. After stirring at 50-55° C. for 2 hr, the mixture was cooled to 40-45° C. and stirred 2 hrs. The resulting slurry was then cooled to room temperature and stirred for 20 hrs. The slurry was filtered, washed with heptanes (30 mL) and dried under vacuum at room temperature to provide Form APO-II Rifaximin (9.8 g).

Example 22

Preparation of Form APO-II Rifaximin

Rifaximin (10 g, KF=0.3%) was dissolved in acetonitrile (30 mL) and water (2.0 mL) with slight heating, and the solution was seeded with Form APO-II. The solution was cooled to room temperature and stirred for 16 hrs. The resulting slurry was filtered, and dried under vacuum at room temperature to provide Form APO-II Rifaximin (7.2 g).

Example 23

Preparation of Form APO-III Rifaximin

Rifaximin Form APO-II (5.0 g) was placed in a filter funnel, washed with water (20 mL) and dried in a vacuum oven at 45-50° C. to afford Form APO-III Rifaximin (4.6 g) (KF=1.1%).

Example 24

Preparation of Form APO-III Rifaximin

Rifaximin Form APO-II (40 g) was placed in a filter funnel and washed with water (160 mL). Approximately one half of the damp solid was dried in a vacuum oven at 40-50° C. to afford Form APO-III Rifaximin (17.1 g) (KF=0.5%).

Example 25

Preparation of Form APO-III Rifaximin

Rifaximin Form APO-II (14 g) was combined with water (30 mL) and stirred at 20-25° C. for 5 min. The slurry was filtered, washed with water (30 mL) and dried in a vacuum oven at 40-50° C. Partially dried solid (3.0 g) was dried further in a vacuum oven at 45-50° C. to afford Form APO-III Rifaximin (3.0 g).

Example 26

Preparation of Form APO-III Rifaximin

Rifaximin Form APO-II (46 g) was placed in a filter funnel and washed with water (250 mL). The damp solid was dried in a vacuum oven at 45-50° C. to afford Form APO-III Rifaximin (41.7 g) (KF=1.8%).

Example 27

Preparation of Form APO-IV Rifaximin

Rifaximin Form APO-II (91 g) was placed in a filter funnel and washed with water (450 mL). The damp solid was dried in vacuo using a rotary evaporator with bath temperature 45-50° C. to afford Form APO-IV Rifaximin (80.5 g) (KF=0.7%).

Example 28

Preparation of Form APO-IV Rifaximin

Rifaximin (106 g) was dissolved in ethyl acetate (250 mL) and water (1.5 mL) at 45-50° C. (KF=2.5%) and then cooled to 30-35° C. Form APO-II seeds were added, and the solution was cooled to room temperature and stirred for 16 hrs. The resulting slurry was cooled to 0-5° C. and stirred for 8 hrs. The slurry was filtered and air dried at room temperature for 16 hrs to provide Form APO-II Rifaximin. The Rifaximin Form APO-II filter cake was washed with water (350 mL). The damp solid (117 g) was dried in vacuo using a rotary evaporator with bath temperature 60-65° C. to afford Form APO-IV Rifaximin (87.3 g) (KF=1.0%).

Example 29

Preparation of Form APO-IV Rifaximin

Rifaximin (106 g) was dissolved in ethyl acetate (200 mL) and water (1.0 mL) at 55-60° C. (calculated KF=2.4%) and then cooled to 20-25° C. in the presence of Form APO-II seeds. Stirring at room temperature was continued for 16 hrs. The resulting slurry was cooled to 0-5° C. and stirred for 8 hrs. The slurry was filtered and air dried at room temperature for 16 hrs. The filter cake was washed with water (300 mL), and the damp solid (125 g) was dried in vacuo using a rotary evaporator with bath temperature 60-65° C. to afford Form APO-IV Rifaximin (91.5 g) (KF=1.0%).

Example 30

Preparation of a mixture of Forms APO-III and APO-IV Rifaximin

Rifaximin Form APO-II (64.3 g) was placed in a filter funnel and washed with water (300 mL). The damp solid was dried in vacuo using a rotary evaporator with bath temperature 55-60° C. to afford a mixture of Forms APO-III and APO-IV Rifaximin (58.5 g) (KF=0.8%).

Example 31

Preparation of Form APO-I Rifaximin

Rifaximin Form APO-III (3.0 g) was placed in an open container and was subjected to a controlled atmosphere of 27° C. and 60% relative humidity for 5 days to afford Form APO-I Rifaximin (3.1 g) (KF=6.2%).

Example 32

Preparation of Form APO-I Rifaximin

Rifaximin Form APO-III (15.8 g) was placed in an open container and was subjected to a controlled atmosphere of 45° C. and 75% relative humidity for 4 days to afford Form APO-I Rifaximin (16.8 g) (KF=6.1%).

Example 33

Preparation of Form APO-I Rifaximin

Rifaximin Form APO-IV (10.0 g) was placed in an agitated open container and subjected to a stream of moist nitrogen at an external temperature of about 35° C. for 17 hrs to afford Form APO-I Rifaximin (10.6 g) (KF=5.8%).

Example 34

Preparation of Form APO-I Rifaximin

Rifaximin Form APO-IV (10.0 g) was placed in an agitated open container and subjected to a stream of moist nitrogen at an external temperature of about 20-25° C. for 20 hrs to afford Form APO-I Rifaximin (KF=7.6%).

Example 35

Preparation of Form APO-I Rifaximin

Rifaximin Form APO-IV (10.0 g) was placed in an agitated open container and subjected to a stream of moist nitrogen at an external temperature of about 35° C. for 6 hrs to afford Form APO-I Rifaximin (10.7 g) (KF=5.5%).

Example 36

Preparation of Form APO-I Rifaximin

Rifaximin Form APO-IV (72.8 g) was placed in an agitated open container and subjected to a stream of moist nitrogen at an external temperature of about 20-25° C. for 17 hrs to afford Form APO-I Rifaximin (77.3 g) (KF=6.9%).

Example 37

Preparation of Form APO-I Rifaximin

Rifaximin mixture of Forms APO-III and APO-IV (23.0 g) was placed in an agitated open container and subjected to a stream of moist nitrogen at an external temperature of about 20-25° C. for 16 hrs to afford Form APO-I Rifaximin (24.7 g) (KF=7.4%).

Example 38

Preparation of Form APO-I Rifaximin

Rifaximin mixture of Forms APO-III and APO-IV (40 g) was placed in a fluid bed dryer and subjected to a stream of moist nitrogen at a temperature of about 45-55° C. for 4 hrs to afford Form APO-I Rifaximin (KF=5.6%). The material was then subjected to a stream of dry nitrogen at a temperature of about 45-55° C. for 24 hrs to afford a mixture of Forms APO-III and APO-IV Rifaximin (KF=1.8%). Further exposure to a stream of moist nitrogen at a temperature of about 45-55° C. for 6 hrs to gave Form APO-I Rifaximin (23.7 g) (KF=4.5%).

Example 39

Preparation of Form APO-I Rifaximin

Rifaximin Form APO-IV (60 g) was placed in a fluid bed dryer and subjected to a stream of moist nitrogen at a temperature of about 40-50° C. for 4 hrs to afford Form APO-I Rifaximin (51.3 g) (KF=5.1%).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. A polymorphic form APO-III of Rifaximin characterized by a PXRD diffractogram comprising peaks, in terms of degrees 2-theta, at approximately 7.1, 8.4, 11.6, 13.1, 18.5, 18.8, and 25.0.

2. The polymorphic form of APO-III of Rifaximin of claim 1 wherein the PXRD diffractogram further comprises peaks, in terms of degrees 2-theta, at approximately 9.1, 15.3, 16.4, 19.4.

3. The polymorphic form APO-III of Rifaximin of claim 1 characterized by a PXRD diffractogram substantially similar to the PXRD diffractogram as depicted in FIG. 5.

4. The polymorphic form APO-III of Rifaximin of claim 1 characterized by a 1% KBr FTIR spectrum comprising peaks, in terms of $cm^{-1}$, at approximately 3427, 2968, 2934, 1714, 1648, 1588, 1506, 1373, 1338, 1226, 1158, and 1124.

5. A process for preparation of a polymorphic form APO-III of Rifaximin, the process comprising:
  i. displacing a first organic solvent with water from a polymorphic form APO-II of Rifaximin to produce a damp cake; and
  ii. drying the damp cake until a water content of between about 0.5% to about 2% is reached;
  wherein polymorphic form APO-II of Rifaximin is characterized by a PXRD diffractogram comprising peaks, in terms of degrees 2-theta, at approximately 6.4, 7.0, 7.3, 7.7, 9.0, 11.1, 19.6, and 20.8;
  polymorphic form APO-III of Rifaximin is characterized by a PXRD diffractogram comprising peaks, in terms of degrees 2-theta, at approximately 7.1, 8.4, 11.6, 13.1, 18.5, 18.8, and 25.0; and
  the first organic solvent is selected from the group consisting of ethyl acetate, dichloromethane, isopropanol, n-butanol, acetonitrile, heptanes, and mixtures thereof.

6. The process for preparation of a polymorphic form APO-III of Rifaximin of claim 5 wherein the first organic solvent is ethyl acetate.

7. The process for preparation of a polymorphic form APO-III of Rifaximin of claim 5 wherein the displacing a first organic solvent with water is performed by washing a polymorphic form APO-II of Rifaximin with water, or performed by suspending or pulping a polymorphic form APO-II of Rifaximin in water.

8. The process for preparation of a polymorphic form APO-III of Rifaximin of claim 5 wherein prior to drying the damp cake has a water content of from about 20% to about 50%.

9. The process for preparation of a polymorphic form APO-III of Rifaximin of claim 5 wherein the drying is conducted under vacuum or using a fluid bed dryer, at a temperature of from about 40° C. to about 70° C., and drying proceeds until a water content of about 1.5% is reached.

10. A polymorphic form APO-IV of Rifaximin characterized by a PXRD diffractogram comprising peaks, in terms of degrees 2-theta, at approximately 7.1, 8.3, 8.6, 12.0, 13.4, 16.3, 19.7 and 26.2.

11. The polymorphic form APO-IV of Rifaximin of claim 10 wherein the PXRD diffractogram further comprises peaks, in terms of degrees 2-theta, at approximately 12.9, 13.1, 14.4, 15.7, 19.1, 19.5, and 25.3.

12. The polymorphic form APO-IV of Rifaximin of claim 10 characterized by a PXRD diffractogram substantially similar to the PXRD diffractogram as depicted in FIG. 7.

13. A process for preparation of a polymorphic form APO-IV of Rifaximin, the process comprising:
  i. displacing a second organic solvent with water from a polymorphic form APO-II of Rifaximin to produce a damp cake; and
  ii. drying the damp cake until a water content of less than or equal to about 1.0% is reached;
  wherein polymorphic form APO-II of Rifaximin is characterized by a PXRD diffractogram comprising peaks, in terms of degrees 2-theta, at approximately 6.4, 7.0, 7.3, 7.7, 9.0, 11.1, 19.6, and 20.8;
  polymorphic form APO-IV of Rifaximin is characterized by a PXRD diffractogram comprising peaks, in terms of degrees 2-theta, at approximately 7.1, 8.3, 8.6, 12.0, 13.4, 16.3, 19.7, and 26.2; and
  the second organic solvent is selected from the group consisting of ethyl acetate, dichloromethane, isopropanol, n-butanol, acetonitrile, heptanes, and mixtures thereof.

14. The process for preparation of a polymorphic form APO-IV of Rifaximin of claim 13 wherein the second organic solvent is ethyl acetate.

15. The process for preparation of a polymorphic form APO-IV of Rifaximin of claim 13 wherein the displacing a second organic solvent with water is performed by washing a polymorphic form APO-II of Rifaximin with water, or performed by suspending or pulping a polymorphic form APO-II of Rifaximin in water.

16. The process for preparation of a polymorphic form APO-IV of Rifaximin of claim 13 wherein prior to drying the damp cake has a water content of from about 20% to about 50%.

17. The process for preparation of a polymorphic form APO-IV of Rifaximin of claim 13 wherein the drying is conducted under vacuum or using a fluid bed dryer, at a temperature of from about 40° C. to about 70° C., and drying proceeds until a water content of about 1% is reached.

18. A process for the preparation of a polymorphic form APO-I of Rifaximin, the process comprising exposing polymorphic form APO-III, APO-IV or mixtures thereof to humidity;
  wherein polymorphic form APO-I of Rifaximin is characterized by a PXRD diffractogram comprising peaks, in terms of degrees 2-theta, at approximately 6.7, 7.7, 8.4, 9.6, 12.7, 16.0, and 18.7,
  polymorphic form APO-III of Rifaximin is characterized by a PXRD diffractogram comprising peaks, in terms of degrees 2-theta, at approximately 7.1, 8.4, 11.6, 13.1, 18.5, 18.8, and 25.0; and
  polymorphic form APO-IV of Rifaximin is characterized by a PXRD diffractogram comprising peaks, in terms of degrees 2-theta, at approximately 7.1, 8.3, 8.6, 12.0, 13.4, 16.3, 19.7, and 26.2.

19. The process for the preparation of a polymorphic form APO-I of Rifaximin of claim 18 wherein the APO-III, APO-IV or mixtures thereof are exposed to humidity until the water content of the solid is from about 4.5% to about 8%.

20. The process for the preparation of a polymorphic form APO-I of Rifaximin of claim 18 wherein the exposing a polymorphic form APO-III, APO-IV or mixtures thereof to humidity comprises contacting APO-III, APO-IV or mixtures thereof with a combination of water vapour and an inert gas.

21. A process for preparation of the polymorphic form APO-II of Rifaximin, the process comprising:
   i. preparing a solution comprising Rifaximin, water and a third organic solvent wherein the solution has a water content of from about 0.5% to about 5%; and
   ii. crystallizing polymorphic form APO-II of Rifaximin;
   wherein polymorphic form APO-II of Rifaximin is characterized by a PXRD diffractogram comprising peaks, in terms of degrees 2-theta, at approximately 6.4, 7.0, 7.3, 7.7, 9.0, 11.1, 19.6, and 20.8; and
   the third organic solvent is selected from the group consisting of alcohols, alkyl ethers, alkyl esters, ketones, aromatic hydrocarbons, aliphatic hydrocarbons, halogenated hydrocarbons, and mixtures thereof.

22. The process for preparation of a polymorphic form APO-II of Rifaximin of claim 21 wherein the third organic solvent is selected from the group consisting of methanol, ethanol, propanol, isopropanol, butanol, methyl t-butyl ether, ethyl acetate, butyl acetate, acetone, methyl ethyl ketone, methyl isobutyl ketone, hexanes, heptanes, dichloromethane, and mixtures thereof.

23. The process for preparation of a polymorphic form APO-II of Rifaximin of claim 22 wherein the third organic solvent is ethyl acetate.

24. The process for preparation of a polymorphic form APO-II of Rifaximin of claim 21 wherein the water content is from about 1% to about 3%.

25. The process for preparation of a polymorphic form APO-II of Rifaximin of claim 21 wherein the water content is from about 2.1% to about 2.7%.

\* \* \* \* \*